United States Patent
Kang et al.

(10) Patent No.: US 11,903,718 B2
(45) Date of Patent: Feb. 20, 2024

(54) AUTOMATIC NOISE SIGNAL INTERVAL DETECTION METHOD AND DEVICE

(71) Applicant: IMEDISYNC. LTD., Seoul (KR)

(72) Inventors: Seung Wan Kang, Seoul (KR); Ukebo Park, Seoul (KR)

(73) Assignee: IMEDISYNC, LTD., Seoul (KR)

( * ) Notice: Subject to any disclaimer, the term of this patent is extended or adjusted under 35 U.S.C. 154(b) by 0 days.

(21) Appl. No.: 18/027,572

(22) PCT Filed: Dec. 2, 2021

(86) PCT No.: PCT/KR2021/018058
§ 371 (c)(1),
(2) Date: Mar. 21, 2023

(87) PCT Pub. No.: WO2022/260228
PCT Pub. Date: Dec. 15, 2022

(65) Prior Publication Data
US 2023/0255538 A1    Aug. 17, 2023

(30) Foreign Application Priority Data
Jun. 9, 2021   (KR) .......................... 10-2021-0074930

(51) Int. Cl.
*A61B 5/374* (2021.01)

(52) U.S. Cl.
CPC .................................... *A61B 5/374* (2021.01)

(58) Field of Classification Search
CPC ..... A61B 5/374; A61B 5/4088; A61B 5/7207; A61B 5/7217; A61B 5/369; A61B 5/7203
See application file for complete search history.

(56) References Cited

U.S. PATENT DOCUMENTS

| 11,154,229 | B2* | 10/2021 | Das .................... A61B 5/369 |
| 2014/0163627 | A1* | 6/2014 | Starr ................ A61M 5/1723 607/45 |
| 2015/0351641 | A1* | 12/2015 | Kang .................. A61B 5/4058 600/301 |

(Continued)

FOREIGN PATENT DOCUMENTS

| KR | 10-2010-0114256 | 10/2010 |
| KR | 10-2011-0087501 | 8/2011 |

(Continued)

OTHER PUBLICATIONS

Nolan et al. "FASTER: Fully Automated Statistical Thresholding for EEG artifact Rejection", whole document (Year: 2010).*
Kim et al. "An effective feature extraction method by power spectral density of EEG signal for 2-class motor imagery-based BCI", whole document (Year: 2017).*
Roy et al. "Deep learning-based electroencephalography analysis: a systematic review", whole document (Year: 2019).*

(Continued)

*Primary Examiner* — Eyob Hagos
(74) *Attorney, Agent, or Firm* — Fish & Richardson P.C.

(57) ABSTRACT

An automatic noise signal interval detection method and device are provided, and the method includes receiving input data and generating initial data in a time-frequency domain, calculating power for each epoch for each channel of the initial data, generating a power graph for a specific frequency region of each channel based on the power for each epoch, generating a baseline based on an average of each channel value on the power graph, and determining, as a noise signal interval, an interval exceeding a predetermined threshold based on the baseline on the power graph.

11 Claims, 13 Drawing Sheets

(56) References Cited

U.S. PATENT DOCUMENTS

| | | | |
|---|---|---|---|
| 2019/0143073 A1* | 5/2019 | Grossman | G16H 10/00 |
| | | | 600/28 |
| 2021/0112139 A1* | 4/2021 | Alsina | H04L 63/102 |
| 2021/0166577 A1* | 6/2021 | Hong | A61M 21/02 |
| 2022/0079507 A1* | 3/2022 | Epelbaum | A61B 5/7235 |
| 2022/0167908 A1* | 6/2022 | D'Arcy | A61B 5/398 |

FOREIGN PATENT DOCUMENTS

| | | | |
|---|---|---|---|
| KR | 10-2018-0060237 | 6/2018 | |
| KR | 10-2019-0059364 | 5/2019 | |
| WO | WO-2020054918 A1 * | 3/2020 | A61B 5/316 |

OTHER PUBLICATIONS

International Search Report and Written Opinion in International Appln. No. PCT/KR2021/018058, dated May 19, 2022, 13 pages (with English translation).

Leske et al., "Reducing Power Line Noise in EEG and MEG Data via Spectrum Interpolation," NeuroImage, Apr. 2019, 189:763-776.

Nolan et al., "FASTER: Fully Automated Statistical Thresholding for EEG artifact Rejection," Journal of Neuroscience Methods, Sep. 2010, 192(1):152-162.

Roy et al., "Deep Learning-Based Electroencephalography Analysis: A Systematic Review," Journal of Neural Engineering, Aug. 2019, 16, 45 pages.

* cited by examiner

AUTOMATIC NOISE SIGNAL INTERVAL DETECTION METHOD AND DEVICE

CROSS-REFERENCE TO RELATED APPLICATIONS

This application is a National Stage application under 35 U.S.C. § 371 of International Application No. PCT/KR2021/018058, filed on Dec. 2, 2021, which claims priority to Korean Application No. 10-2021-0074930, filed on Jun. 9, 2021, the entire contents of both of which are considered part of the disclosure of this application, and are incorporated by reference in their entirety into this application.

BACKGROUND

Field of the Invention

The present invention relates to a technique for detecting and rejecting noise, and more particularly, to an automatic noise signal interval detection method and device for detecting noise based on flow change in frequency power values by converting time-series data into a frequency domain.

Related Art

A biosignal is a combination of various signals and may have a significant effect on analysis results unless it is not subjected to a noise rejection process. In particular, since time-series data very sensitively responds to patterns such as a subject's state and movement, a noise rejection process is very important.

A general process of analyzing a biosignal is divided into a preprocessing step and an analysis step. In the preprocessing step, a process of refining data necessary for analysis is performed, and a noise rejection process is included therein.

Electroencephalogram (EEG) signals measured from the human brain can be acquired through electrodes in contact with the scalp, and at this time, various signals such as resistance in the hair and skin, muscle movement of a subject, and the like are also measured. Accordingly, signals other than EEG are regarded as noise, and accurate analysis values can be derived only when noise is rejected in the preprocessing step.

Types of noise can be classified into electrooculography, electromyogram, an electrocardiogram, and non-physiological artifacts, in general. Accordingly, there is a process of rejecting noise by principal component analysis (PCA) and independent component analysis (ICA), which reflect signal characteristics of noise, but the types and causes of noise corresponding to motion are very diverse. Therefore, it is very difficult to implement the noise by an automation algorithm.

That is, for the reliability, consistency, and accuracy of biosignal analysis results, the process of detecting and rejecting noise corresponding to motion is very important.

The technique used in EEG analysis mainly uses a calculation method that calculates and quantifies in the frequency domain. At this time, the types of brainwaves can be classified into frequency bands. For example, delta waves are classified as 0.5 to 4 Hz, theta waves are classified as 4 to 7 Hz, alpha waves are classified as 8 to 12 Hz, sensory motor rhythm (SMR) waves are classified as 12 to 15 Hz, and beta waves are classified as 15 to 18 Hz, and high beta waves are classified as 18 Hz or higher. In particular, the theta waves appear mainly when drowsiness comes during wakefulness and can significantly affect wakefulness brainwave analysis.

In particular, dementia (or cognitive impairment) may occur in the human brain with aging, and at this time, there is a variation of theta waves as an important feature of brainwaves. Therefore, if slow waves (delta waves, theta waves, etc.) as noise are not satisfactorily distinguished, there is a high likelihood of generating errors in EEG biomarkers used to determine functionality and degeneration.

Non-physiological artifacts caused by a state and motion of a subject include signals related to drowsiness. Drowsiness is closely related to theta waves, and if it is not correctly detected and rejected, it can have a great influence on analysis.

Korean Patent Laid-open Publication No. 10-2010-0114256 relates to a brainwave measurement method and device capable of receiving EEG signals and noise signals and detecting only actual EEG frequencies from which noise has been rejected at the time of measuring EEG at a place where general external noise exists other than a sealed room of a medical institution, and the like when magnitudes of brainwaves are low and thus brainwave sensing is considerably affected by external noise, sensing environment, etc.

Prior Art Literature

Patent Literature

Korean Patent Laid-open Publication No. 10-2019-0059364 (2019.05.31)
Korean Patent Laid-open Publication No. 10-2010-0114256 (2010.10.25)

SUMMARY

An embodiment of the present invention is to provide an automatic noise signal interval detection method and device for detecting noise based on flow change in frequency power values by converting time-series data into a frequency domain.

An embodiment of the present invention is to provide an automatic signal interval detection method and device capable of expecting a mechanism applicable to the same type of noise in various biosignals as well as brainwaves, automatically detecting and rejecting noise signal intervals to increase the reliability and accuracy of analysis results, and reducing accessibility in various fields in which research and application are difficult due to low expertise to achieve application to various researches and developments.

In embodiments, an automatic noise signal interval detection method includes receiving input data and generating initial data in a time-frequency domain, calculating power for each epoch for each channel of the initial data, generating a power graph for a specific frequency region of each channel based on the power for each epoch, generating a baseline based on an average of each channel value on the power graph, and determining, as a noise signal interval, an interval exceeding a predetermined threshold based on the baseline on the power graph.

The generating of the initial data may include receiving time-series data for each channel as the input data by performing a predetermined preprocessing step based on raw data.

The calculating of the power for each epoch may include setting a predetermined time interval as a window of the epoch, and sequentially calculating the power for each epoch while moving the epoch according to a time axis of the initial data.

The sequentially calculating of the power for each epoch may include setting a movement interval of the epoch such that the movement interval includes a predetermined ratio of overlapping interval between successive epochs before and after movement.

The generating of the power graph may include determining a delta or theta region with respect to brainwave signals as the specific frequency region and generating a graph of a frequency power flow over time as the power graph.

The generating of the power graph may include selectively applying the frequency power based on absolute power or relative power.

The generating of the baseline may include setting a size and a movement interval of a unit bin for generating the baseline based on a time axis of the power graph, and calculating an average of each channel value for each unit bit while moving according to the movement interval.

The automatic noise signal interval detection method may further include determining the specific frequency region, the threshold, and frequency power of the power graph according to a type of a noise signal.

The determining of the noise signal interval may include, if there is at least one noise signal, individually setting at least one threshold for each noise signal and determining the noise signal interval based on a number of channels exceeding the at least one threshold according to the noise signal.

The determining of the noise signal interval may include a first step of determining the noise signal interval based on absolute power of the frequency power, a second step of determining the noise signal interval based on relative power of the frequency power, a third step of determining the noise signal interval based on an ensemble of the absolute power and the relative power, and a fourth step of finally determining the noise signal interval through a combination of the first to third steps.

The automatic noise signal interval detection method may further include rejecting a noise rejection interval defined based on the noise signal interval from the power graph.

The rejecting of the noise rejection interval from the power graph may include determining the noise rejection interval by adding a predetermined margin interval before and after the noise signal interval.

The automatic noise signal interval detection method may further include generating a feature map for each epoch based on the initial data, constructing an independent model for classifying the noise signal interval by learning the feature map for each epoch, and determining a final noise signal interval based on a first noise signal interval classified based on the baseline and a second noise signal interval classified by the independent model.

In embodiments, an automatic noise signal interval detection device include a data converter configured to receive input data and to generate initial data in a time-frequency domain, a data processor configured to calculate power for each epoch for each channel of the initial data, a data analyzer configured to generate a power graph for a specific frequency region of each channel based on the power for each epoch, a baseline generator configured to generate a baseline based on an average of each channel value on the power graph, and a noise signal detector configured to determine, as a noise signal interval, an interval exceeding a predetermined threshold based on the baseline on the power graph.

The disclosed technology has the following effects. However, it does not mean that a specific embodiment should include all of the following effects or only the following effects, and thus it should not be understood that the scope of rights of the disclosed technology is limited thereby.

The automatic noise signal interval detection method and device according to an embodiment of the present invention can detect noise based on flow change in frequency power values by converting time-series data into a frequency domain.

The automatic noise signal interval detection method and device according to an embodiment of the present invention can expect a mechanism applicable to the same type of noise in various biosignals as well as brainwaves, automatically detecting and rejecting noise signal intervals to increase the reliability and accuracy of analysis results, and reducing accessibility in various fields in which research and application are difficult due to low expertise, to achieve application to various researches and developments.

DESCRIPTION OF EXEMPLARY EMBODIMENTS

Figure 1:
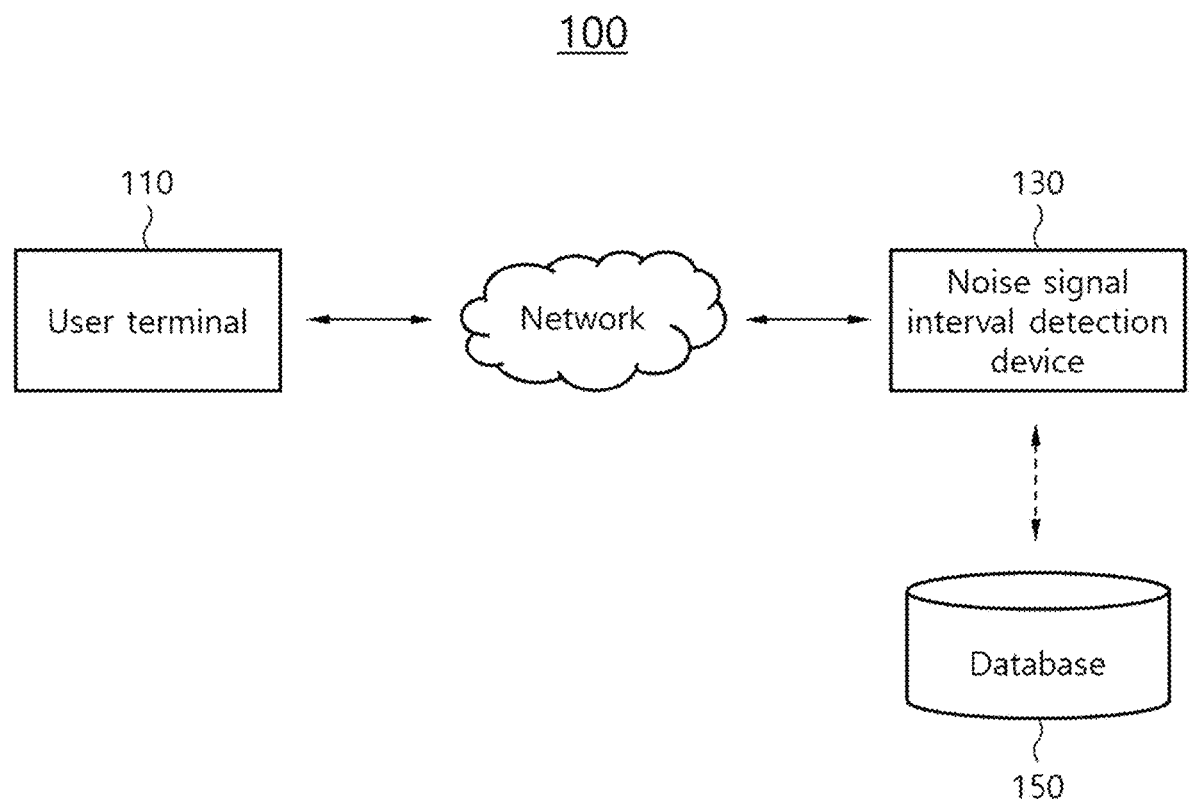
FIG. 1 is a diagram illustrating a noise signal interval detection system according to the present invention.

The description of the present disclosure is merely an example for structural or functional explanation, and the scope of the present disclosure should not be construed as being limited to the embodiments set forth herein. That is, the embodiments are to be construed as being variously embodied and having various forms, so that the scope of the present invention should be understood to include equivalents capable of realizing technical ideas. Also, the purpose or effect of the present invention should not be construed as limiting the scope of the present invention, since it does not mean that a specific embodiment should include all or only such effect.

Meanwhile, the meaning of the terms described in the present application should be understood as follows.

The terms "first", "second", and the like are intended to distinguish one element from another, and the scope of the right should not be limited by these terms. For example, the first component may be referred to as a second component, and similarly, the second component may also be referred to as a first component.

When one element is described as being "connected" to another element, it shall be construed as being connected or accessed to another element directly but also as possibly having yet another element in between. On the other hand, if one element is described as being "directly connected" to another element, it shall be construed that there is no other element in between. This is also true of other expressions for explaining a relationship between elements, i.e., "between" and "directly between" or "adjacent to" and "directly adjacent to".

Unless clearly used otherwise, expressions in the singular number include a plural meaning. In the present description, an expression such as "comprising", "including", or "having" is intended to designate a characteristic, a number, a step, an operation, an element, a part or combinations thereof, and shall not be construed to preclude any presence or possibility of one or more other characteristics, numbers, steps, operations, elements, parts or combinations thereof.

Identification codes (e.g., a, b, and c) of each step are merely used for better comprehension and ease of description, not indicating a specific order of the steps, and the steps may be performed in a different order from a described order, unless clearly limited otherwise. Specifically, the steps may be performed in the same order as the described order, may substantially simultaneously be performed, or may be performed in the reverse order.

The present disclosure may be embodied as computer-readable code in a computer readable recording medium, and the computer-readable recording medium may include all kinds of recording devices for storing data that is readable by a computer system. Examples of the computer-readable recording medium include a ROM, a RAM, a CD-ROM, a magnetic tape, a floppy disk, an optical data storage device, and the like. Further, the computer-readable recording medium may be distributed to a computer system connected via a network and thus store and execute computer-readable code in a distributed manner.

Unless otherwise defined, all terms used herein have the same meaning as how they are generally understood by those of ordinary skill in the art to which the disclosure pertains. Any term that is defined in a general dictionary shall be construed to have the same meaning in the context of the relevant art, and, unless otherwise defined explicitly, shall not be interpreted to have an idealistic or excessively formalistic meaning.

FIG. 1 is a diagram illustrating a noise signal interval detection system according to the present invention.

Referring to FIG. 1, the noise signal interval detection system 100 may include a user terminal 110, a noise signal interval detection device 130, and a database 150.

The user terminal 110 may correspond to a computing device capable of collecting and providing biosignals measured from a user. That is, the user can collect or measure biosignals such as his/her brainwaves and heartbeats through the user terminal 110 and transmit collected information to the noise signal interval detection system 100 for noise rejection.

In addition, the user terminal 110 may be implemented as a smartphone, a laptop computer, or a computer that is operable by being connected to the noise signal interval detection device 130, and is not necessarily limited thereto and may be implemented as various devices such as a tablet PC. The user terminal 110 may be connected to the noise signal interval detection device 130 through a network, and a plurality of user terminals 110 may be simultaneously connected to the noise signal interval detection device 130. In addition, a dedicated program or application capable of using a predetermined service provided by the noise signal interval detection system 100 may be installed and executed in the user terminal 110.

The noise signal interval detection device 130 may be implemented as a server corresponding to a computer or a program capable of generating cleaned signals by rejecting noise based on biosignals measured from the user. The noise signal interval detection device 130 may be connected to the user terminal 110 through a wired network or a wireless network such as Bluetooth or Wi-Fi, and may transmit/receive data to/from the user terminal 110 through the network. In addition, the noise signal interval detection device 130 may be implemented to operate in association with a separate external system (not shown in FIG. 1) to collect data or provide additional functions.

Unlike FIG. 1, the noise signal interval detection device 130 may be included in the user terminal 110. In this case, the noise signal interval detection device 130 may be implemented as an independent module that performs an automatic noise signal interval detection method according to the present invention as one component of the user terminal 110. Here, for clearer understanding, the noise signal interval detection device 130 will be described as a device independent of the user terminal 110.

The database 150 may correspond to a storage device for storing various types of information necessary for the operation of the noise signal interval detection device 130. For example, the database 150 may store information on biosignals collected or measured from the user and may store information for preprocessing of biosignals, but is not necessarily limited thereto and may store information collected or processed in various forms in a process in which the noise signal interval detection device 130 performs the automatic noise signal interval detection method.

Further, the database 150 is shown as a device independent of the noise signal interval detection device 130 in FIG. 1, but is not necessarily limited thereto and may be included in the noise signal interval detection device 130 as a logical storage device of the noise signal interval detection device 130.

Figure 2:
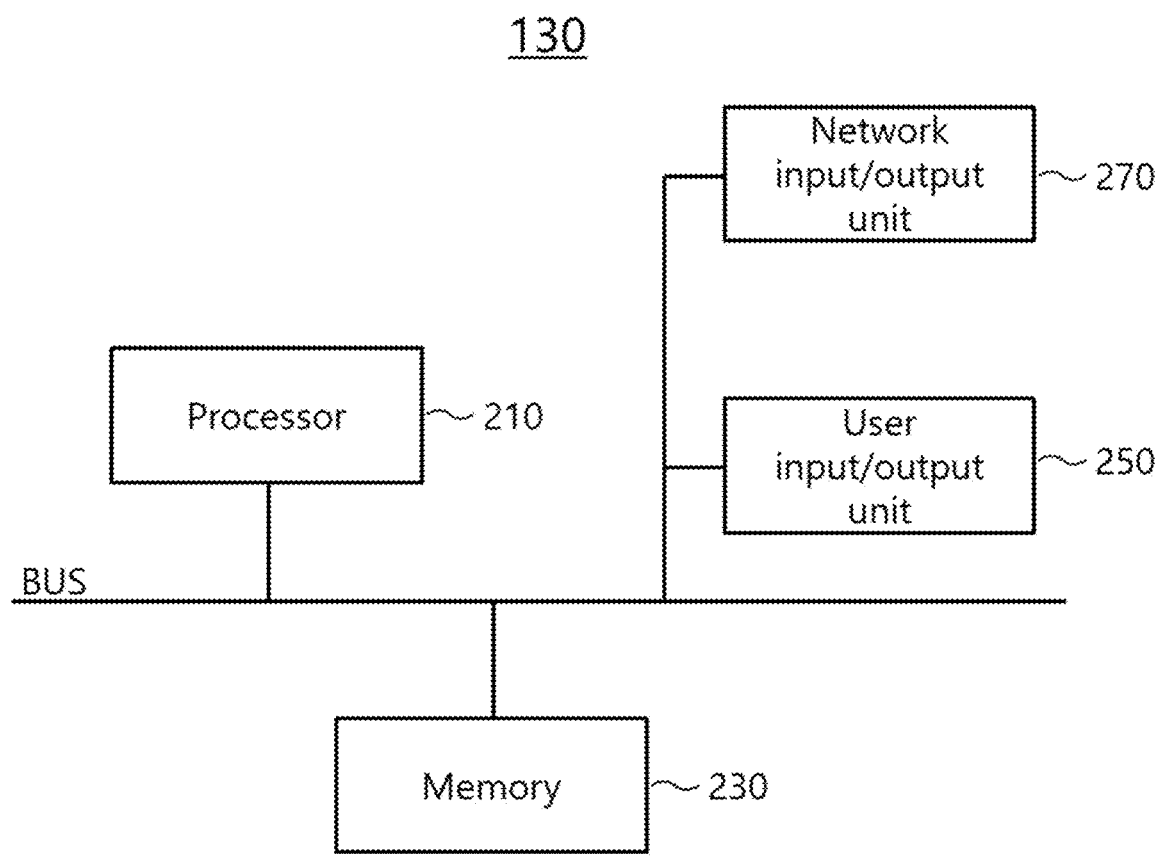
FIG. 2 is a diagram illustrating a system configuration of a noise signal interval detection device of FIG. 1.

FIG. 2 is a diagram illustrating a system configuration of the noise signal interval detection device of FIG. 1.

Referring to FIG. 2, the noise signal interval detection device 130 may include a processor 210, a memory 230, a user input/output unit 250, and a network input/output unit 270.

The processor 210 may execute a procedure for processing each step in the operation process of the noise signal interval detection device 130, manage the memory 230 read or written throughout the process, and schedule synchronization time between a volatile memory and a non-volatile memory included in the memory 230. The processor 210 may control the overall operation of the noise signal interval detection device 130 and may be electrically connected to the memory 230, the user input/output unit 250, and the network input/output unit 270 to control data flows therebetween. The processor 210 may be implemented as a central processing unit (CPU) of the noise signal interval detection device 130.

The memory 230 may include an auxiliary storage device that is implemented as a non-volatile memory such as a solid state drive (SSD) or a hard disk drive (HDD) and used to store data necessary for the noise signal interval detection device 130 and may include a main storage device implemented as a volatile memory such as a random access memory (RAM).

The user input/output unit 250 may include an environment for receiving user input and an environment for outputting specific information to the user. For example, the user input/output unit 250 may include an input device including an adapter such as a touch pad, a touch screen, an on-screen keyboard, or a pointing device, and an output device including an adapter such as a monitor or a touch screen. In one embodiment, the user input/output unit 250 may correspond to a computing device connected through remote access, and in such a case, the noise signal interval detection device 130 may serve as an independent server.

The network input/output unit 270 includes an environment for connecting to an external device or system through a network and may include, for example, an adapter for communication, such as a local area network (LAN), a metropolitan area network (MAN), a wide area network (WAN), and a value added network (VAN).

Figure 3:
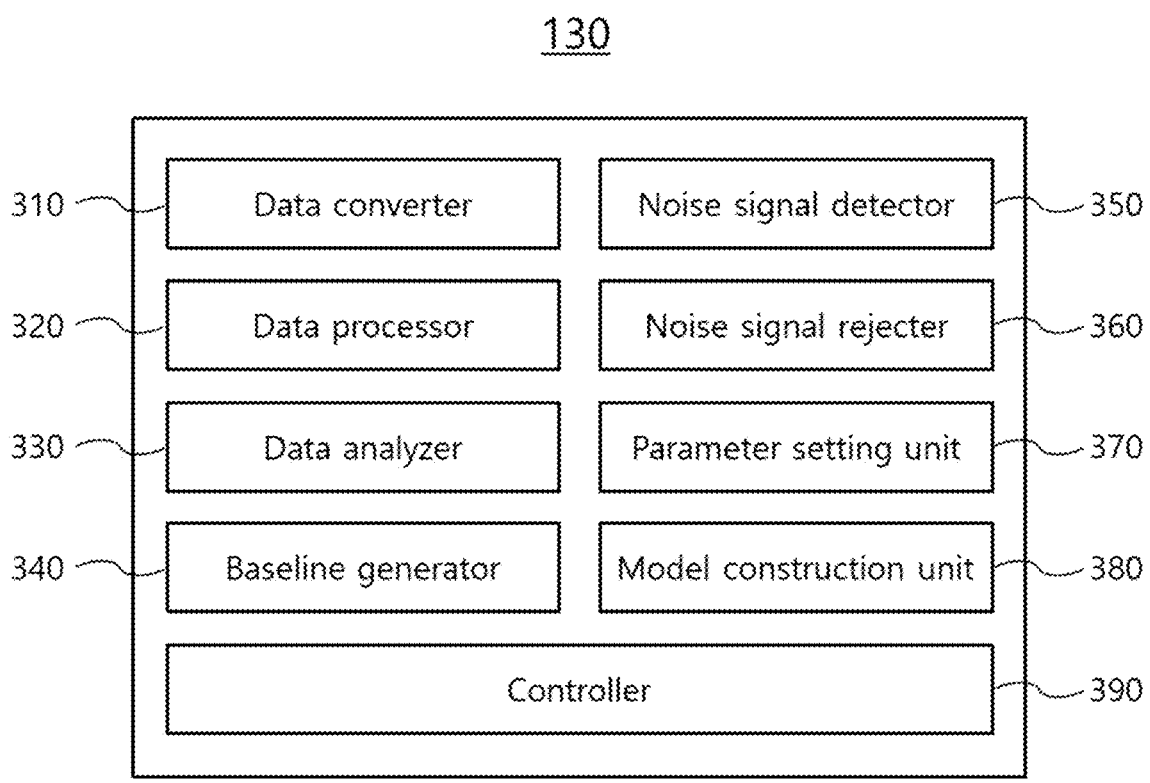
FIG. 3 is a diagram illustrating a functional configuration of the noise signal interval detection device of FIG. 1.

FIG. 3 is a diagram illustrating a functional configuration of the noise signal interval detection device of FIG. 1.

Referring to FIG. 3, the noise signal interval detection device 130 includes a data converter 310, a data processor 320, a data analyzer 330, a baseline generator 340, and a noise signal detector 350, a noise signal rejecter 360, a parameter setting unit 370, a model construction unit 380, and a controller 390.

The data converter 310 may receive input data and generate initial data in a time-frequency domain. The data converter 310 may receive biosignal (e.g., EEG signals) including noise collected from the user, wherein the biosignals correspond to time-series data regarding a flow of signal intensity over time. The data converter 310 may convert time-series data into frequency domain data such that a noise signal interval detection operation using frequency power can be performed.

More specifically, the data converter 310 may utilize a Superlet method applied based on Fast Fourier Transform (FFT) as a method of converting time-series domain data into frequency domain data. The Superlet method has strength in temporal resolution compared to an FFT method and may be suitable to calculate frequency power within a short interval. Meanwhile, the data converter 310 may use the Superlet method for data conversion, but it is not necessarily limited thereto and various methods capable of performing computation in the frequency domain may be used. The data converter 310 may selectively convert frequency domain data into time-frequency data.

In one embodiment, the data converter 310 may receive time-series data with respect to each channel as input data by performing a predetermined preprocessing step based on raw data. That is, input data transmitted to the data converter 310 may correspond to cleaned data from which noise has been primarily rejected by a predetermined preprocessing operation. This will be described in more detail with reference to FIG. 5.

The data processor 320 may calculate power for each epoch for each channel of initial data. Here, the initial data may be composed of signals for a plurality of channels. For example, an EEG signal may be composed of a plurality of signals collected through electrode sensors attached to the head of a user. In particular, EEG signals can be measured through electrodes (Fp1, Fp2, F7, F8, F3, F4, Fz, T3, T4, C3, C4, Cz, T5, T6, P3, P4, Pz, O1, O2) disposed at predetermined positions according to International Standard 10-20 system, and EEG signals collected therefrom may be composed of a total of 19 channels (or frequency bands).

Accordingly, the data processor 320 may perform an independent operation for each channel of the initial data. In one embodiment, the data processor 320 may set a predetermined time interval as an epoch window and may sequentially calculate power for each epoch while moving epochs along the time axis of the initial data.

First, the data processor 320 may determine an epoch window for calculating a power spectrum density (PSD). Here, an epoch may correspond to a time unit for calculating frequency power. That is, the epoch window may be defined as a predetermined time interval, and may be set to, for example, 4 seconds. Meanwhile, the epoch window may be variably applied according to characteristics of raw data.

When the epoch window is set, the data processor 320 may sequentially extract signal intervals corresponding to the epoch window along the time axis of the initial data and calculate the frequency power density (PSD) based on the signal intervals. That is, the data processor 320 may repeatedly perform an operation of calculating epoch band power from initial data after setting the epoch window.

In one embodiment, the data processor 320 may set an epoch movement interval such that an overlapping interval by a predetermined ratio is included between successive moving epochs. For example, when an overlapping ratio is set to 90%, the data processor 320 may set an epoch movement interval such that 90% overlapping occurs for each epoch interval (overlapping windowing). That is, when the epoch window is 4 seconds and the overlapping ratio is 90%, if the first epoch interval is 0 to 4 s, the second interval may correspond to 0.4 to 4.4 s. Meanwhile, the overlapping ratio between epochs may be variably applied. The power for each epoch (PSD for each interval) calculated by the data processor 320 may include information on a frequency power flow over time.

In one embodiment, the data processor 320 may generate a feature map for each epoch based on initial data. That is, the data processor 320 may generate a feature map for each epoch for each channel of the initial data. The data processor may calculate power for each epoch based on the initial data and generate the power for each epoch as a visualized image. That is, the feature map for each epoch may correspond to an image generated by visualizing the power for each epoch. Feature maps generated by the data processor 320 may be used as training data to construct an independent model for detecting noise signal intervals.

The data analyzer 330 may generate a power graph for a specific frequency region of each channel based on the power for each epoch. In one embodiment, the data analyzer 330 may determine a delta or theta region of EEG signals as a specific frequency region and generate a graph regarding a frequency power flow over time as a power graph. For example, when slow drift caused by a drowsiness interval or a specific motion is detected by analyzing EEG signals of a user, power flows in delta and theta frequency bands of EEG signal channels may be important.

Accordingly, the data analyzer 330 may determine the delta or theta region as a specific frequency region and extract power information of the corresponding frequency band from the power of each epoch to generate a power graph. Here, the power graph may be represented as a graph regarding a frequency power flow over time. That is, the power graph may correspond to a two-dimensional graph having an x-axis and a y-axis, in which the x-axis may be represented as a time axis and the y-axis may be represented as a PSD axis.

In one embodiment, the data analyzer 330 may apply frequency power as absolute power or relative power. Here, absolute power may be calculated through the sum of power values (e.g., degrees of appearances of a plurality of EEG signals) of a plurality of preprocessed EEG signals. In addition, relative power may be calculated through a ratio (%) occupied by a power value of each of the plurality of preprocessed EEG signals in the total sum of power values of the plurality of preprocessed EEG signals. However, the method of calculating the absolute power and the relative power is not necessarily limited thereto, and various methods may be applied.

Accordingly, the y-axis of the power graph may correspond to a PSD value with respect to delta or theta, which may be generated based on absolute power or relative power. The noise signal interval detection device 130 may selectively apply absolute power or relative power of the power graph according to characteristics of a noise signal to be detected.

For example, when first noise (e.g., drowsiness interval noise) and second noise (e.g., specific motion interval noise) which are different are classified based on absolute power (PSD Abs) or relative power (PSD Rel), the second noise can be satisfactorily classified when relative power PSD is used as a reference, and the first noise can be satisfactorily classified when the absolute power PSD is used as a reference. That is, both absolute power and relative power can be used for each noise, and noise may be classified according to an ensemble of absolute power and relative power.

The baseline generator 340 may generate a baseline based on the average of channel values on the power graph. Here, the baseline may correspond to a reference line for classifying noise, and a frequency power trend for each channel may be rejected through the baseline. The baseline generator 340 may generate a baseline for detecting a noise signal based on information on integration of frequency powers of a plurality of channels constituting basic data. In this case, the baseline generator 340 may generate a baseline through the average of channel values, but is not limited thereto and various methods may be used to integrate channel values.

Figure 7:
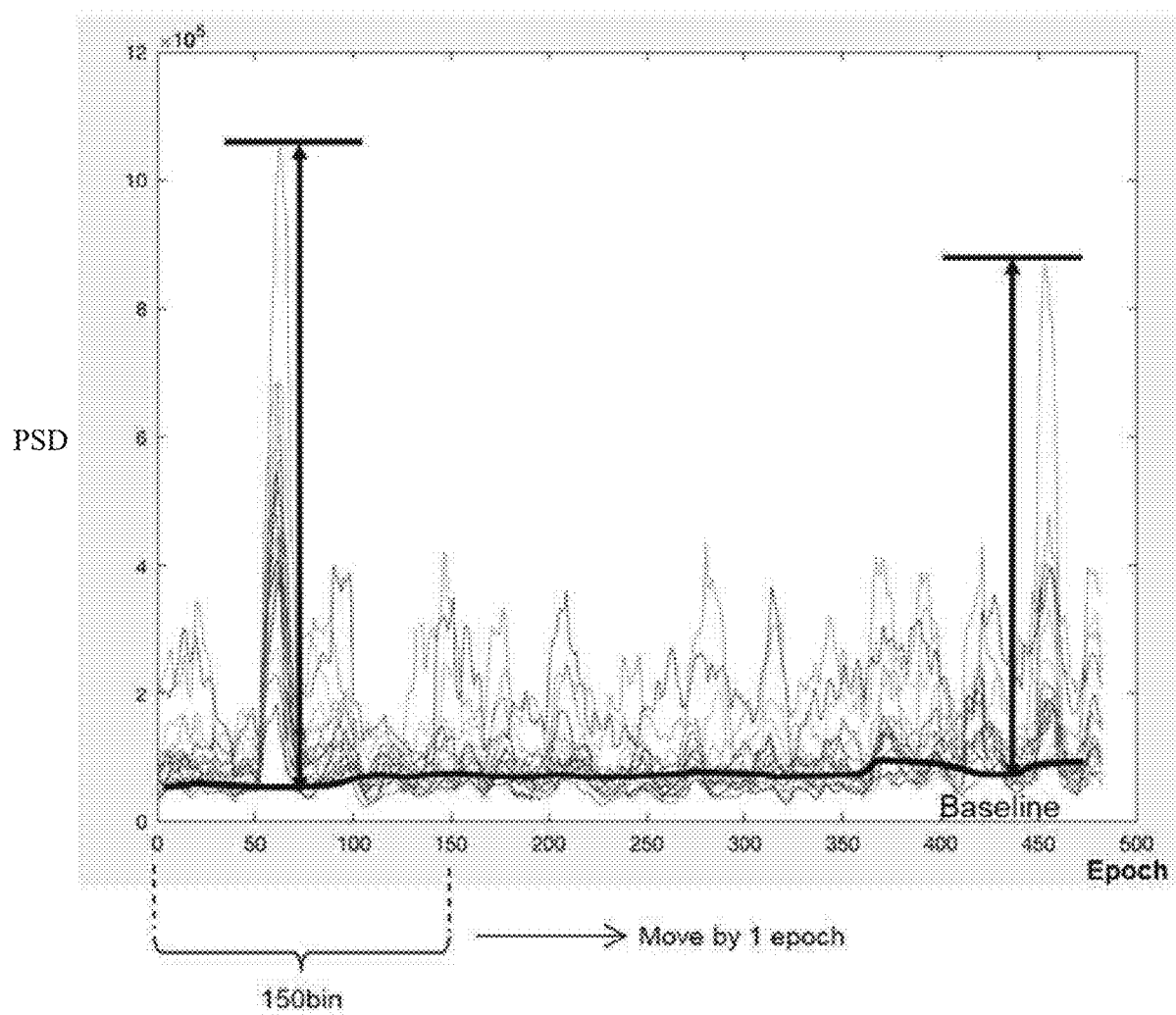
FIG. 7 is a diagram illustrating a baseline according to the present invention.

In one embodiment, the baseline generator 340 may set a size and a movement interval of a unit interval for generating a baseline based on the time axis of the power graph and calculate the value of channel values for each unit interval while moving according to the movement interval. For example, as shown in FIG. 7, the baseline generator 340 generates a baseline based on a specific range (e.g., 150 bins) with respect to the entire range (500 epochs in the case of FIG. 7). Further, the baseline generator 340 may generate a baseline while moving the unit interval by 1 epoch interval.

At this time, when the size of the bin is reduced, sensitivity to PSD change can increase, and on the contrary, when the size of the bin is increased, robustness to PSD change can increase. In FIG. 7, when a PSD is generated based on a window of 4 seconds and 90% overlapping for EEG data having a length of 3 minutes and 20 seconds (200 seconds), PSD data having a total of 500 epochs can be generated. In addition, a bin may correspond to a criterion for determining x values used to calculate the average of the baseline. Sensitivity to PSD change can be increased as a bin value increases, and robustness to PSD change can be increased as a bin value decreases.

The noise signal detector 350 may determine, as a noise signal interval, an interval exceeding a preset threshold based on the baseline on the power graph. That is, the noise signal detector 350 may determine a time region exceeding the threshold based on the baseline as a noise signal interval (bad epoch region).

In one embodiment, the noise signal detector 350 may individually set at least one threshold for each noise signal when there is at least one noise signal, and based on the number of channels exceeding the at least one threshold, determine a noise signal interval according to the noise signal. That is, a threshold may be independently set for each noise signal in order to identify noises, and a plurality of thresholds may be set for the same noise signal if necessary. In general, since the first noise (drowsiness interval noise) and the second noise (specific motion interval noise) have different magnitudes, different thresholds need to be determined for respective noises.

TABLE 1

| Division | First noise | | Second noise | | Presence or absence of noise |
| --- | --- | --- | --- | --- | --- |
| | First threshold 1.5 | Number of channels 4 | Second threshold 2 | Number of channels 2 | |
| Data 1 | | 3 | | 0 | × |
| Data 2 | | 3 | | 1 | ○ (first noise) |
| Data 3 | | 6 | | 0 | ○ (first noise) |
| Data 4 | | 3 | | 2 | ○ (second noise) |

For example, referring to Table 1 above, when the number of channels exceeding a first threshold for the first noise is set to 4, if the number of channels exceeding the first threshold in actual data is 4 or more, the data can be determined as the first noise, but if the number of channels exceeding the first threshold is less than 4, the data cannot be determined as the first noise.

As another example, on the assumption that a second threshold greater than the first threshold is set in case of detecting the second noise along with the first noise, 1) if the number of channels exceeding the first threshold in actual data is 3 (no channel exceeds the second threshold), the data is not determined as noise (data 1 in Table 1), and 2) the data is determined as noise if the number of channels exceeding the first threshold is 3 and the number of channels exceeding the second threshold is 1, the noise can be identified as the first noise (data 2 in Table 1). In addition, 3) if the number of channels exceeding the first threshold is 6 and there is no channel exceeding the second threshold, the data is determined as noise and the noise can be identified as the first noise (data 3 in Table 1).

If the number of channels exceeding the second threshold is set to 2, 4) the data is determined as noise if the number of channels exceeding the first threshold is 2 and the number of channels exceeding the second threshold is 2, and the noise can be identified as the second noise (data 4 in Table 1). That is, the noise signal detector 350 may set a plurality of threshold criteria for each noise signal, and set the number of channels exceeding each threshold such that the number is in inverse proportion to the magnitudes of the threshold criteria.

In one embodiment, the noise signal detector 350 may determine a noise signal interval based on various combinations of absolute or relative power of frequency power. That is, the noise signal detector 350 may basically determine a noise signal interval by applying a single criterion of absolute power or noise power, and may determine a noise signal interval based on an ensemble of absolute and relative powers if necessary. For example, the noise signal detector 350 may primarily check whether corresponding data is the first noise based on absolute power, and then finally check whether the data is the first noise based on relative power to define a noise signal interval. However, the operation of the noise signal detector 350 is not limited to the aforementioned order, and relative power may be checked first and then absolute power may be checked, or noise may be checked according to the ensemble of absolute power and relative power.

More specifically, the noise signal detector 350 may perform a first step of determining a noise signal interval based on absolute power of frequency power, a second step of determining a noise signal interval based on relative power of the frequency power, a third step of determining a noise signal interval based on an ensemble of the relative power and the absolute power, and a fourth step of finally determining a noise signal interval through a combination of the first to third steps.

In one embodiment, the noise signal detector 350 may determine a final noise signal interval based on a first noise signal interval classified based on the baseline and a second noise signal interval classified by an independent model. The noise signal detector 350 may detect a noise signal interval based on the baseline based on the PSD, but a method of detecting a noise signal interval through an image may also be applied. That is, the noise signal detector 350 may detect a noise signal interval using an independent model constructed on the basis of a feature map for each epoch as visualized information. An independent model may be generated as a result of learning a feature map for each epoch, which may be performed by a model construction unit 380. This will be described in more detail with reference to FIG. 10.

The noise signal rejecter 360 may reject a noise rejection interval defined based on a noise signal interval from the power graph. In one embodiment, the noise signal rejecter 360 may determine a noise rejection interval by adding a predetermined margin before and after a noise signal interval.

In rejection of a noise signal interval, if only an interval in which noise is severely deformed is locally rejected, signal disconnection may occur, which may affect an EEG analysis algorithm. Therefore, the noise signal rejecter 360 may re-specify a rejection interval such that it can sufficiently include the start and end of waveforms related to a noise signal by adding an extra interval before/after the noise signal interval. Here, the noise rejection interval may correspond to an interval re-specified for signal rejection. This will be described in more detail with reference to FIG. 9.

The parameter setting unit 370 may determine a specific frequency region, a threshold, and frequency power of a power graph according to the type of a noise signal. That is, the noise signal interval detection device 130 may set various parameters for noise signal detection through the parameter setting unit 370. The parameter setting unit 370 may individually set thresholds according to characteristics of noise to be detected. In addition, the parameter setting unit 370 may also change the frequency region of a reference PSD or criteria for absolute power and relative power according to noise.

The model construction unit 380 may construct an independent model for classifying noise signal intervals by learning a feature map for each epoch. This will be described in more detail in FIG. 10.

The controller 390 may control the overall operation of the noise signal interval detection device 130 and manage control flows or data flows between the data converter 310, the data processor 320, the data analyzer 330, the baseline generator 340, the noise signal detector 350, the noise signal rejecter 360, the parameter setting unit 370, and the model construction unit 380.

Figure 4:
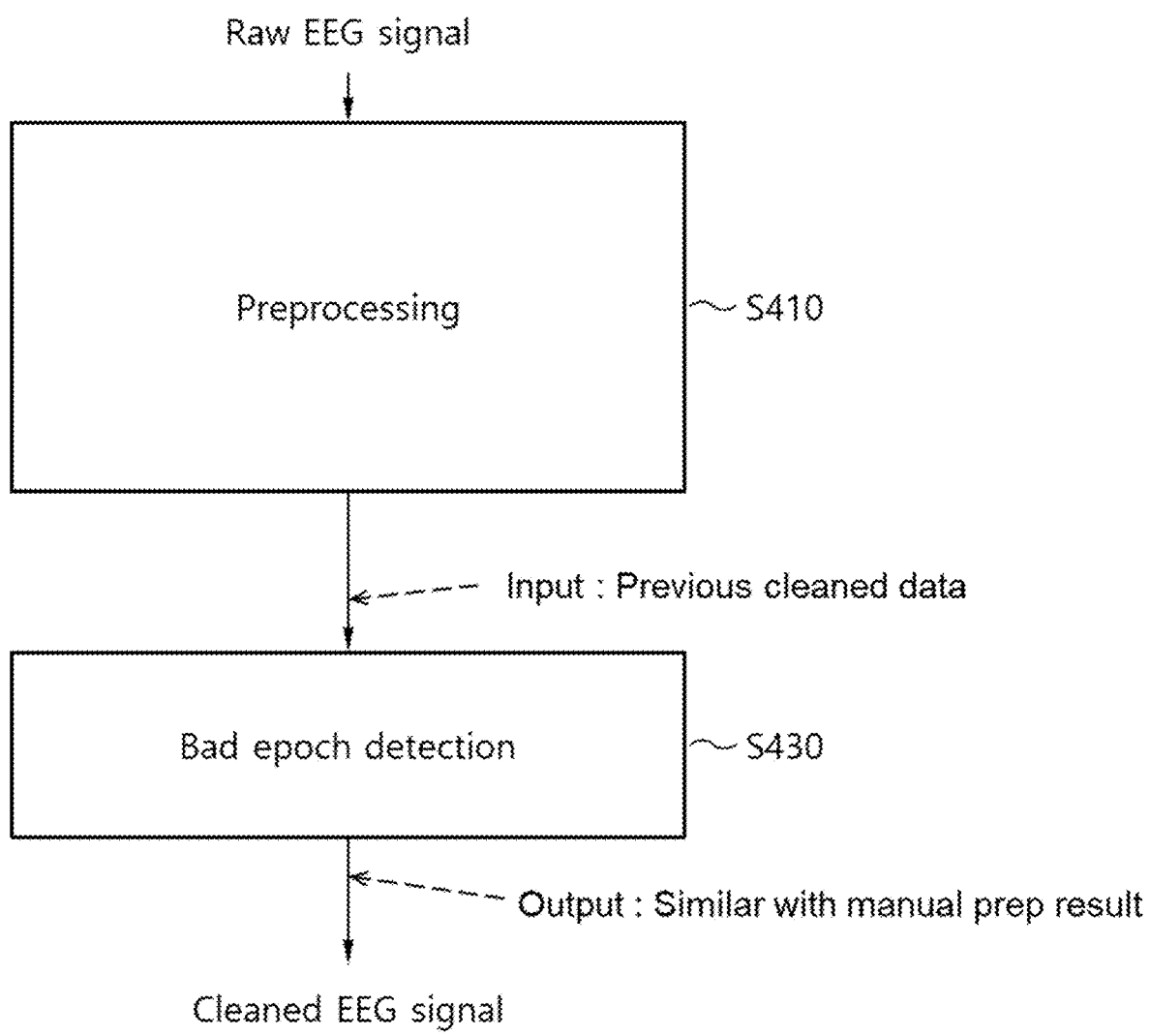
FIG. 4 is a flowchart illustrating a noise signal rejection method to which an automatic noise signal interval detection method according to the present invention is applied.

FIG. 4 is a flowchart illustrating a noise signal rejection method to which the automatic noise signal interval detection method according to the present invention is applied.

Referring to FIG. 4, the noise signal interval detection device 130 may perform a preprocessing operation for detecting a noise signal interval based on biosignals measured from a user (S410). For example, in case of measuring a raw EEG signal of a subject, the noise signal interval detection device 130 is not limited to a specific device and may measure the EEG signal through various devices.

In particular, since an EEG signal has a very fine magnitude in unit of μV, it needs to be greatly amplified and accurately measured. In addition, the EEG signal may be affected by eye movements and muscle activities of a user, external devices, and the like.

Therefore, measurement of an EEG signal can be started only when the resistance between electrodes of an electroencephalogram and the human scalp is a certain standard or less. In the step of measuring and collecting EEG signals, an operation of reducing impedance (to 5 kΩ or less), such as removing foreign substances between the user's scalp and electrodes and combing the user's hair, may be required.

Preferably, the user needs to be in an awake resting state and brainwaves need to be measured in a sitting state. A data sampling rate for EEG data needs to be 200 Hz or higher and must be extracted in the form of raw data.

In addition, the noise signal interval detection device 130 may perform filtering in a frequency range in which time-series signals of raw data will be analyzed and interpreted. Analysis is mainly performed at 1 to 45 Hz, but the frequency range is not limited.

The reason for filtering signals below 1 Hz is that the transition of signals between 0 and 1 Hz is considerable and the range is very sensitive to noise. In addition, it may correspond to a range generally excluded from analysis targets as analysis results.

The noise signal interval detection device 130 may selectively perform notch filtering as necessary. For example, in the case of Korea, there is AC power noise of 55 or 60 Hz, and the AC power noise may be different for each country and region. The noise signal interval detection device 130 may then sequentially perform predetermined preprocessing operations, and as a result, receive time-series data from which noise has been primarily rejected as input data and start an operation for detecting a noise signal interval (S430).

Figure 5:
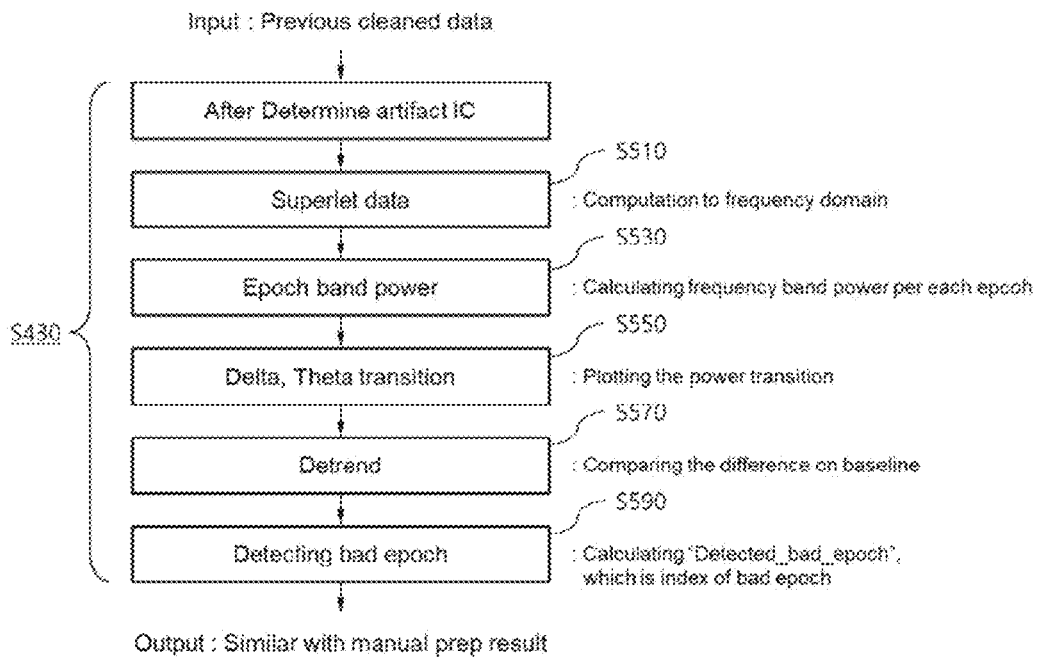
FIG. 5 is a flowchart illustrating the automatic noise signal interval detection method according to the present invention.

FIG. 5 is a flowchart illustrating the automatic noise signal interval detection method according to the present invention.

Referring to FIG. 5, the noise signal interval detection device 130 may specifically perform an operation for detecting a noise signal interval based on input data received through a predetermined preprocessing step as described above with reference to FIG. 4.

More specifically, the noise signal interval detection device 130 may perform an operation of converting input data into basic data of the frequency domain through a Superlet data step (S510).

Thereafter, the noise signal interval detection device 130 may calculate power for each epoch from the basic data through an epoch band power step (S530). The noise signal interval detection device 130 may generate a power graph for a specific frequency region based on power for each epoch through a delta and theta transition step (S550).

Thereafter, the noise signal interval detection device 130 may generate a baseline as a result of integrating signals of each channel on the power graph through a detrend step (S570). The noise signal interval detection device 130 may detect a noise signal interval through comparison with the baseline through a detecting bad epoch step (S590).

FIGS. 6a to 6d are diagrams illustrating general frequency flows of slow drift in a drowsiness interval and a specific motion interval.

Referring to FIGS. 6a to 6d, the noise signal interval detection device 130 may generate a power graph for a specific frequency region of each channel based on power for each epoch through the data analyzer 330. That is, it is possible to ascertain a frequency power flow over time through the power graph. In particular, a power flow in the delta and theta frequency bands may be important in detecting slow drift generated according to a drowsiness interval and a specific motion. FIG. 6 show a general frequency flow phenomenon with respect to such slow drift.

Figure 6A:
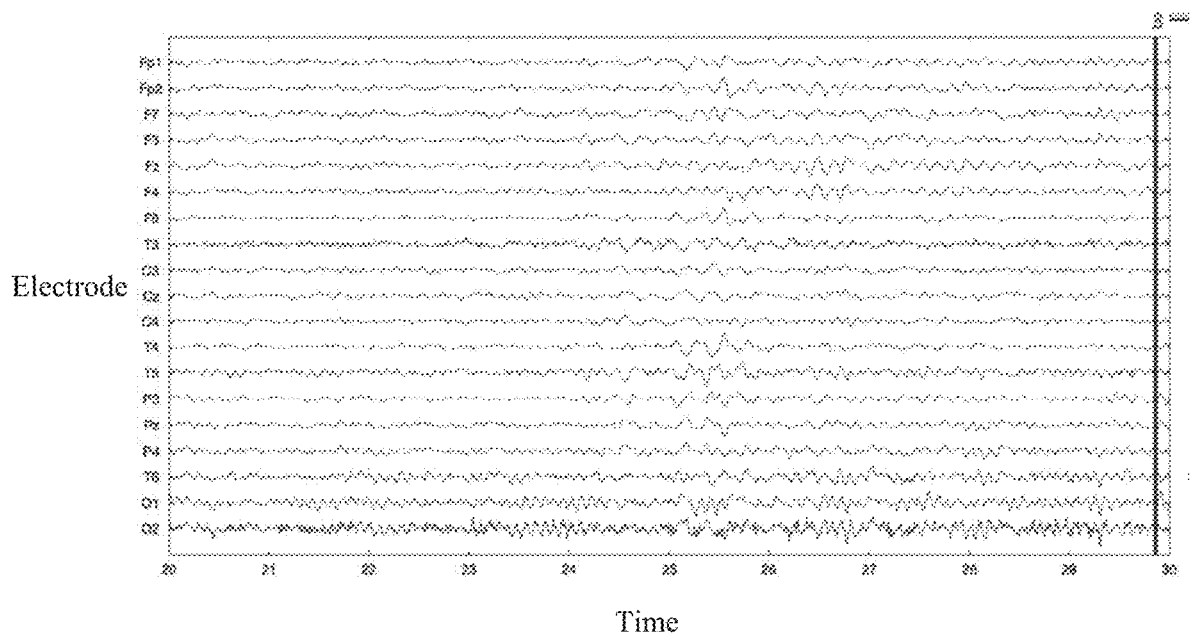
FIGS. 6a to 6d are diagrams illustrating general frequency flows of slow drift in a drowsiness interval and a specific motion interval.
Figure 6B:
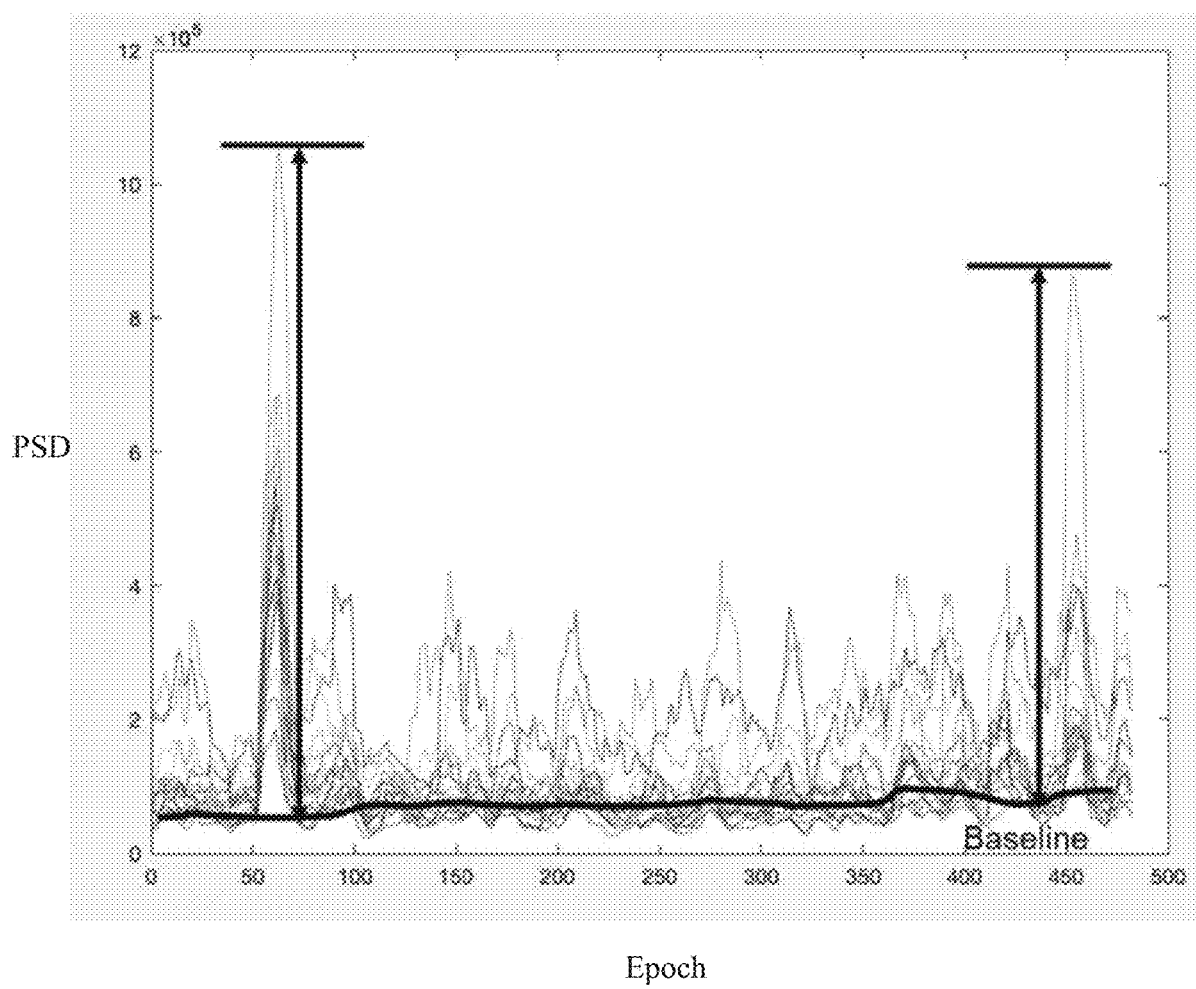

More specifically, FIG. 6a shows input data for drowsiness interval noise (first noise), and FIG. 6b may correspond to delta or theta PSD data for the drowsiness interval noise. That is, it can be confirmed that a large flow change occurs in most electrodes within power flows of delta and theta at the same time.

Figure 6C:
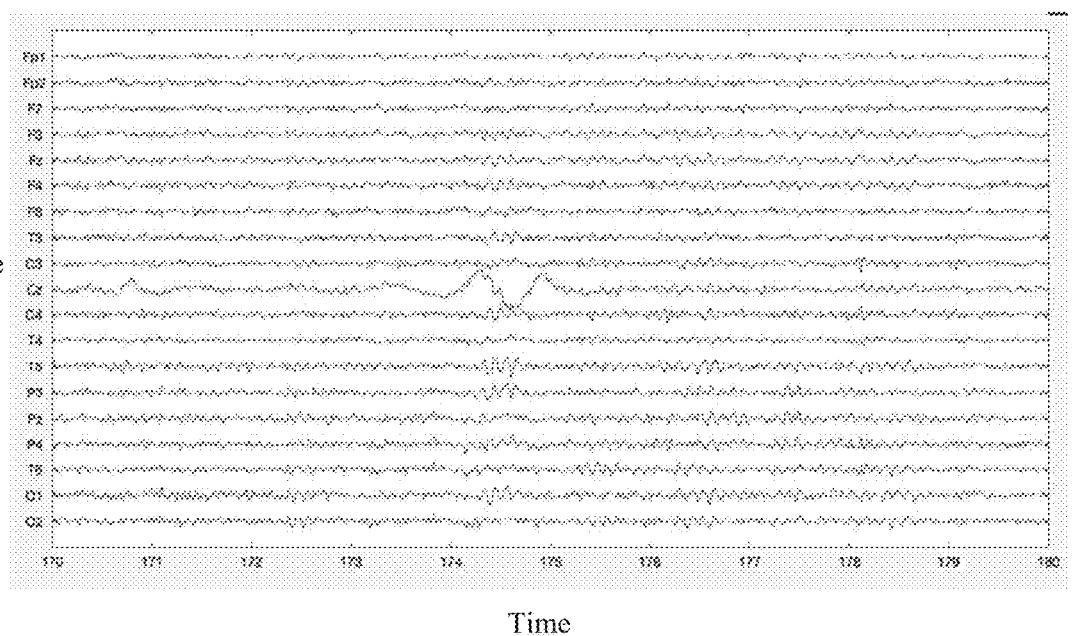
Figure 6D:
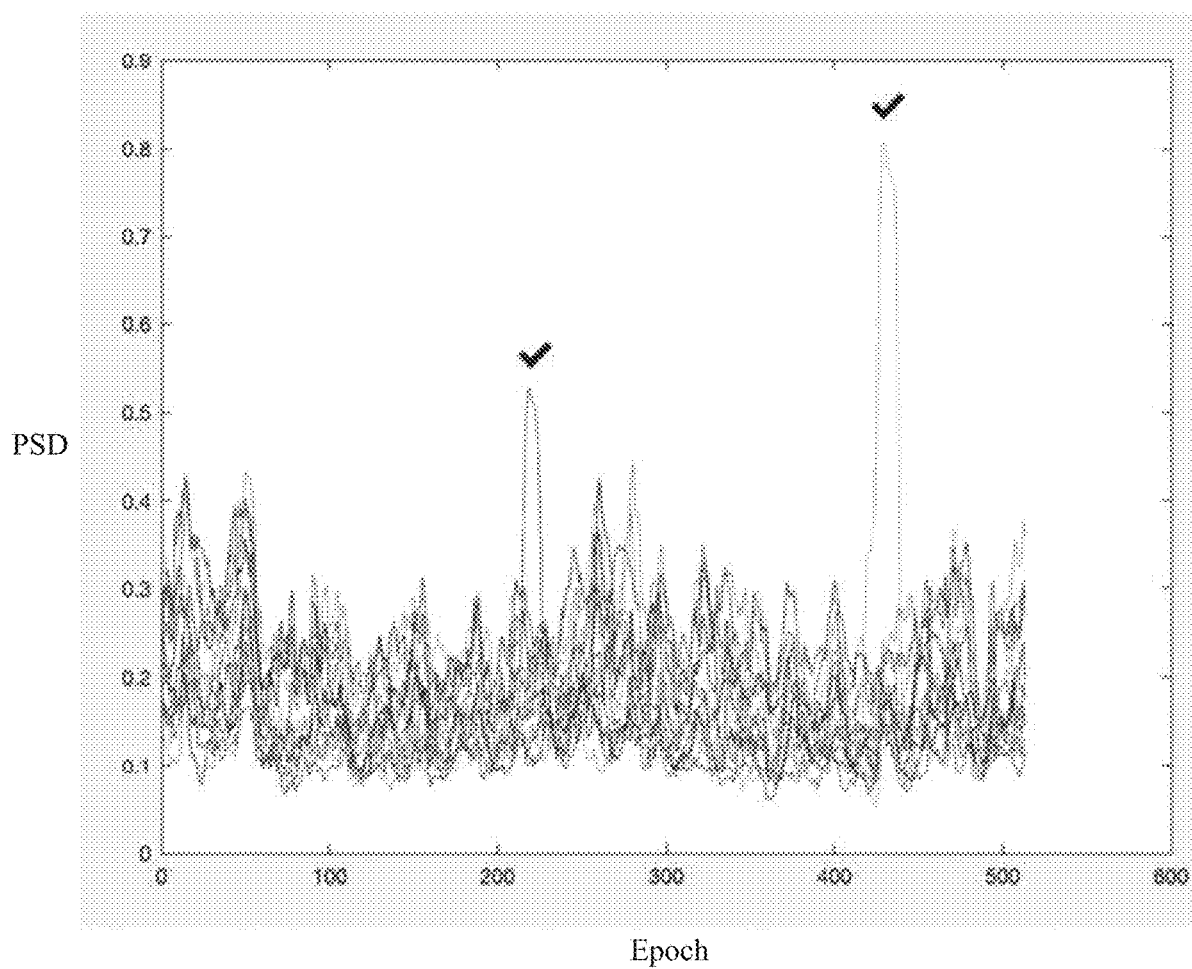

FIG. 6c shows input data for specific motion interval noise (second noise), and FIG. 6d may correspond to delta or theta PSD data for the specific motion interval noise. That is, it can be confirmed that a very large change occurs in a specific electrode within the power flow of delta or theta, unlike flows in other electrodes.

FIG. 8 is a diagram illustrating absolute power and relative power of frequency power.

Figure 8A:
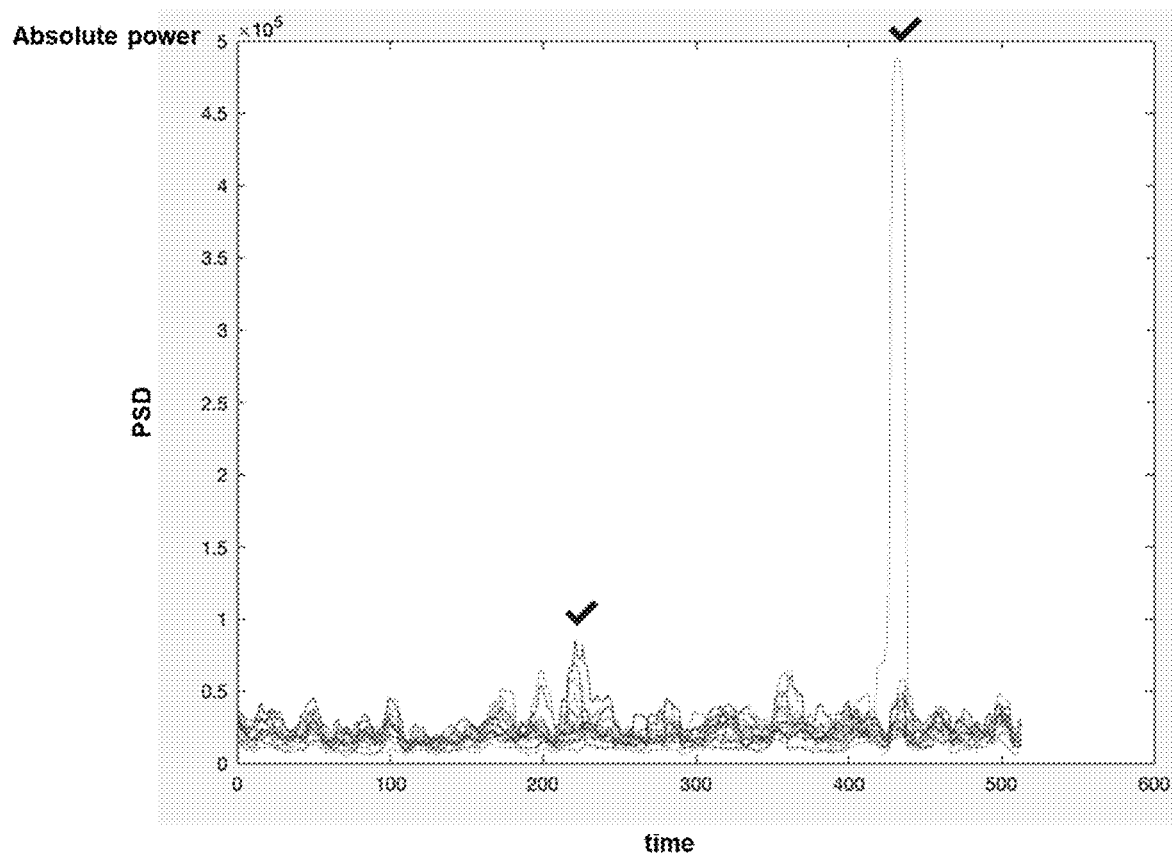
FIGS. 8a and 8b are diagrams illustrating absolute power and relative power of frequency power.
Figure 8B:
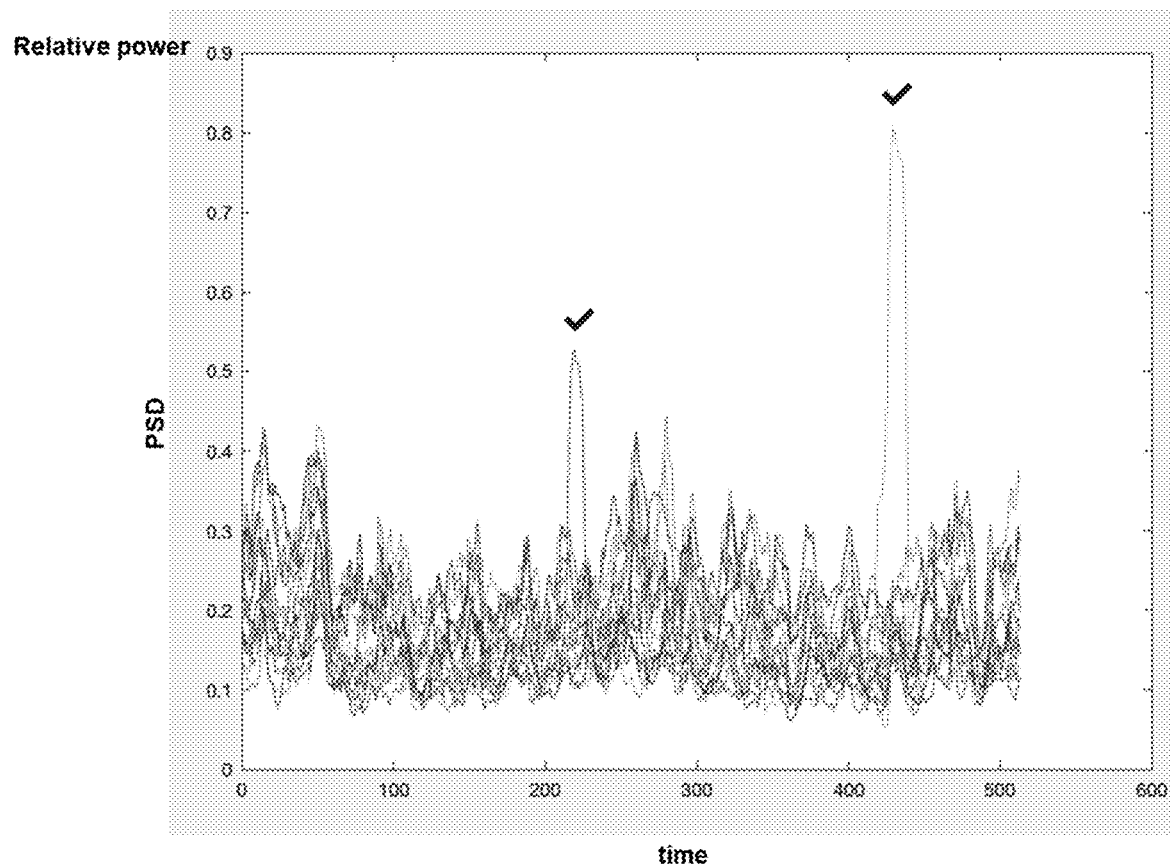

Referring to FIG. 8, the noise signal interval detection device 130 may determine a noise signal interval based on various combinations of absolute or relative power of frequency power through the noise signal detector 350. FIG. 8a shows a process of applying a threshold for detecting a noise signal interval based on absolute power, and FIG. 8b shows a process of applying a threshold for detecting a noise signal interval based on relative power.

The thresholds may change according to the first noise (drowsiness interval noise) and the second noise (specific motion interval noise). In addition, the frequency region of reference PSD or absolute (Abs) and relative (Rel) standards may also be changed.

Here, criteria for detecting a bad epoch may be formed as an ensemble. For example, a bad epoch may be defined by primarily checking whether corresponding data is the first noise based on absolute power and then finally checking whether the data is the first noise based on relative power.

The present invention is not limited to the above order, and relative power may be checked first and then absolute power may be checked, or noise may be checked by an ensemble of the absolute power and the relative power.

Figure 9:
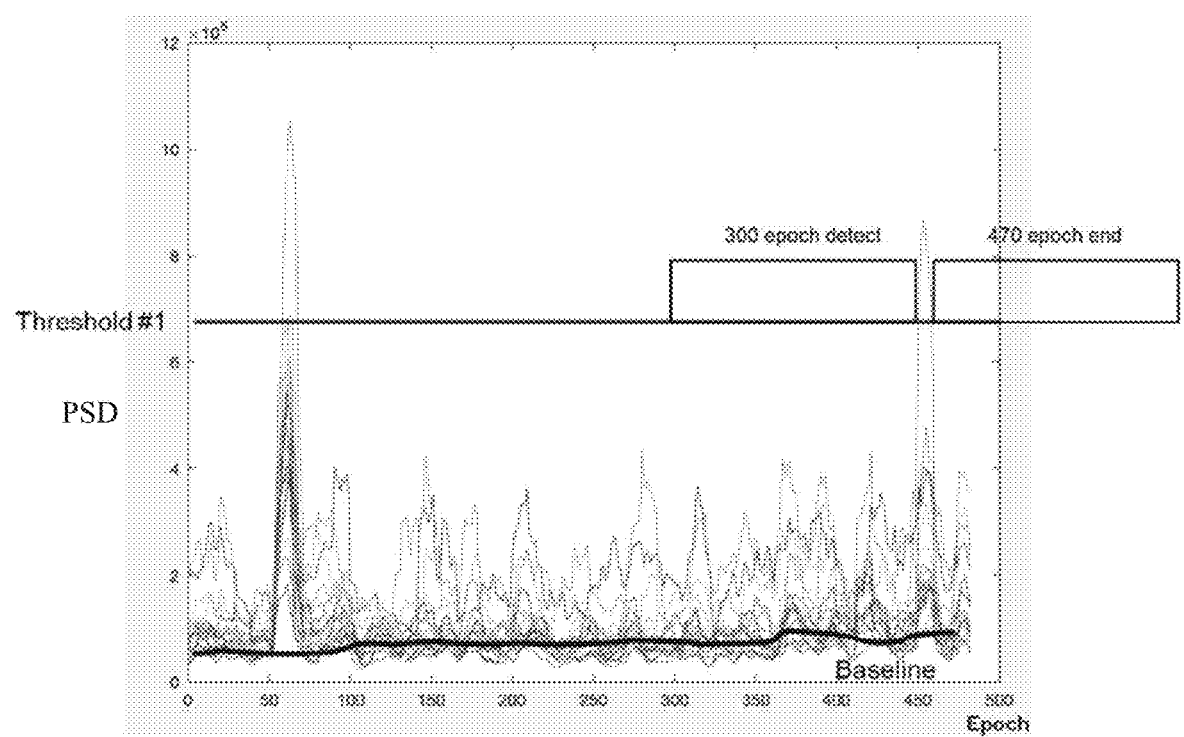
FIG. 9 is a diagram illustrating a noise signal interval according to the present invention.

FIG. 9 is a diagram illustrating a noise signal interval according to the present invention.

Referring to FIG. 9, the noise signal interval detection device 130 may reject a noise rejection interval defined based on a noise signal interval from a power graph through the noise signal rejecter 360.

More specifically, a criterion for setting an interval may be required in order to reject a specified noise signal interval. In rejecting an interval, if only an interval in which noise is severely deformed is locally rejected, signal disconnection occurs, which may affect the subsequent EEG analysis algorithm. Accordingly, the interval is re-specified such that it sufficiently include the start and end of noise signal waves by adding an extra interval before/after the interval.

In FIG. 9, when the bin size is 150, if noise is detected at 300 epoch, the noise starts at 450 epoch, and if it ends at 470 epoch, the noise disappears at 470 epoch, and thus an interval of 450 to 470 epochs can be determined as a noise signal interval (0.4*20=8 seconds in total). Therefore, the noise signal interval detection device 130 does not reject exactly 8 seconds but may add a specific time (e.g., 180 seconds) before and after the interval and reject the interval.

Figure 10:
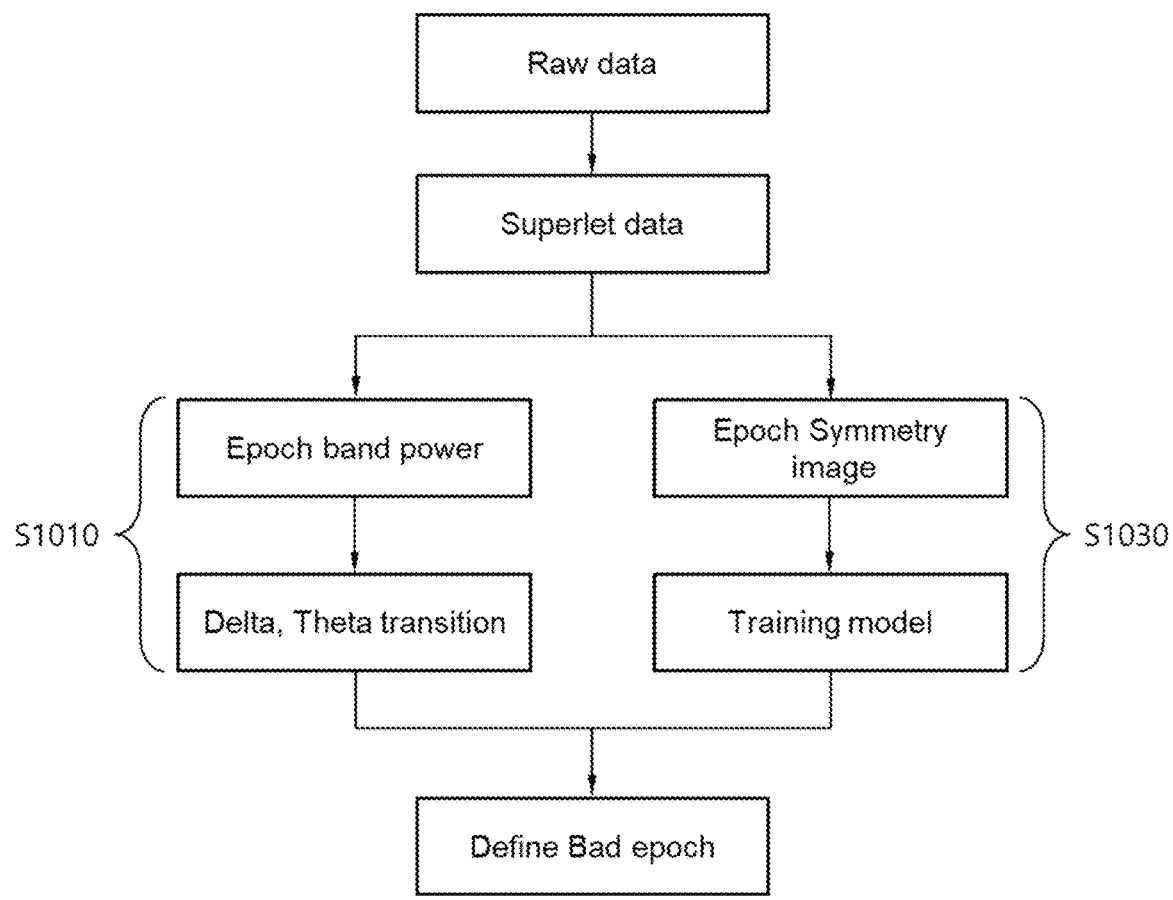
FIG. 10 is a flowchart illustrating a method of detecting a noise signal interval based on a PSD and an image according to the present invention.

FIG. 10 is a flowchart illustrating a method of detecting a noise signal interval based on a PSD and an image according to the present invention.

Referring to FIG. 10, the noise signal interval detection method according to the present invention can be applied to various types of noise. That is, the noise signal interval detection may correspond to a method applicable to various biosignals using time-series data in addition to brainwaves.

In addition, the noise signal interval detection method may be a method of detecting a bad epoch through an image instead of only using a PSD (i.e., an ensemble method).

In FIG. 10, the noise signal interval detection method according to the present invention may detect a noise signal interval by integrally applying a PSD-based noise signal detection process (first process, S1010) and an image-based noise signal detection process (second process, S1030). That is, the first process and the second process are independently performed, and as a result of integrating noise signal intervals detected in the respective processes, a final noise signal interval can be determined.

Although the present invention has been described above with reference to a preferred embodiment, those skilled in the art can understand that the present invention can be modified and changed in various manners without departing from the spirit and scope of the present invention described in the claims.

REFERENCE SIGNS LIST

100: Noise signal interval detection system
110: User terminal 130: Noise signal interval detection device
150: Database
210: Processor 230: Memory
250: User input/output unit 270: Network input/output unit
310: Data converter 320: Data processor
330: Data analyzer 340: Baseline generator
350: Noise signal detector 360: Noise signal rejecter
370: Parameter setting unit 380: Model construction unit
390: Controller

What is claimed is:

1. An automatic noise signal interval detection method performed in an automatic signal interval detection device including a data converter, a data processor, a data analyzer, a baseline generator, and a noise signal detector, the automatic noise signal interval detection method comprising:
receiving input electroencephalogram (EEG) data and generating initial data in a time-frequency domain through the data converter;
calculating power for each epoch for each channel of the initial data through the data processor;
generating a power graph for a specific frequency region of each channel over time using the power for each epoch through the data analyzer, wherein the generating of the power graph comprises (i) determining a delta or theta region with respect to brainwave signals as the specific frequency region and (ii) generating a graph of a frequency power over time as the power graph;

generating a baseline by calculating an average of each channel value on the power graph through the baseline generator;

determining, as a noise signal interval, an interval exceeding a predetermined threshold based on the baseline on the power graph through the noise signal detector, wherein the determining as the noise signal interval comprises:

individually setting at least one threshold for each noise signal if there is at least one noise signal, wherein individually setting the at least one threshold for each noise signal if there is at least one noise signal comprises setting at least a first threshold for a drowsiness interval noise and a second threshold for a specific motion interval noise, and determining the noise signal interval based on the number of channels exceeding the at least one threshold according to the noise signal; and generating a post-processed signal, wherein generating the post-processed signal comprises rejecting the at least one noise signal within the determined noise signal interval.

2. The automatic noise signal interval detection method of claim 1, wherein the generating of the initial data comprises receiving time-series data for each channel as the input electroencephalogram (EEG) data by performing a predetermined preprocessing step based on raw data.

3. The automatic noise signal interval detection method of claim 1, wherein the calculating of the power for each epoch comprises:

setting a predetermined time interval as a window of the epoch; and sequentially calculating the power for each epoch while moving the epoch according to a time axis of the initial data.

4. The automatic noise signal interval detection method of claim 3, wherein the sequentially calculating of the power for each epoch comprises setting a movement interval of the epoch such that the movement interval includes a predetermined ratio of overlapping interval between successive epochs before and after movement.

5. The automatic noise signal interval detection method of claim 1, wherein the generating of the power graph comprises selectively applying the frequency power based on absolute power or relative power.

6. The automatic noise signal interval detection method of claim 1, wherein the generating of the baseline comprises:

setting a size and a movement interval of a unit bin for generating the baseline based on a time axis of the power graph; and calculating an average of each channel value for each unit bit while moving according to the movement interval.

7. The automatic noise signal interval detection method of claim 1, further comprising determining the specific frequency region, the predetermined threshold, and the frequency power of the power graph according to a type of noise.

8. The automatic noise signal interval detection method of claim 7, wherein the determining of the noise signal interval comprises:

a first step of determining the noise signal interval by checking presence or absence of noise according to absolute power of the frequency power;

a second step of determining the noise signal interval by checking presence or absence of noise according to relative power of the frequency power;

a third step of determining the noise signal interval by checking presence or absence of noise according to an ensemble of the absolute power and the relative power; and a fourth step of finally determining the noise signal interval through a combination of the first to third steps.

9. The automatic noise signal interval detection method of claim 1, wherein rejecting the at least one noise signal within the determined noise signal interval comprises adding a predetermined specific interval before and after the noise signal interval and determining the added specific interval and the noise signal interval as the noise rejection interval.

10. The automatic noise signal interval detection method of claim 1, further comprising:

generating a feature map for each epoch corresponding to an image generated by calculating power for each epoch for each channel of the initial data and visualizing the power for each epoch;

constructing a learning model for classifying the noise signal interval by learning the feature map for each epoch as training data; and determining a final noise signal interval using at least one of a first noise signal interval classified based on the baseline and a second noise signal interval classified by the learning model.

11. An automatic noise signal interval detection device comprising:

a data converter configured to receive input electroencephalogram (EEG) data and to generate initial data in a time-frequency domain;

a data processor configured to calculate power for each epoch for each channel of the initial data;

a data analyzer configured to generate a power graph for a specific frequency region of each channel over time using the power for each epoch, wherein the generating of the power graph comprises (i) determining a delta or theta region with respect to brainwave signals as the specific frequency region and (ii) generating a graph of a frequency power over time as the power graph;

a baseline generator configured to generate a baseline by calculating an average of each channel value on the power graph;

a noise signal detector configured to determine, as a noise signal interval, an interval exceeding a predetermined threshold based on the baseline on the power graph, wherein the noise signal detector individually sets at least one threshold for each noise signal if there is at least one noise signal and determines the noise signal interval based on the number of channels exceeding the at least one threshold according to the noise signal, and wherein the at least one threshold for each noise signal individually set by the noise signal detector comprises at least a first threshold for a drowsiness interval noise and a second threshold for a specific motion interval noise; and a noise signal rejecter configured to generate a post-processed signal, wherein generating the post-processed signal comprises rejecting the at least one noise signal within the determined noise signal interval.

* * * * *